United States Patent [19]

Glaser et al.

[11] Patent Number: 5,371,181
[45] Date of Patent: Dec. 6, 1994

[54] THIOL-ENE COMPOSITIONS WITH IMPROVED CURE SPEED RETENTION

[75] Inventors: David M. Glaser, New Britain; Anthony F. Jacobine, Meriden; Paul J. Grabek, Deep River, all of Conn.

[73] Assignee: Loctite Corporation, Hartford, Conn.

[21] Appl. No.: 81,078

[22] Filed: Jun. 22, 1993

Related U.S. Application Data

[63] Continuation-in-part of Ser. No. 619,068, Nov. 28, 1990, and a continuation-in-part of Ser. No. 56,128, Apr. 30, 1993, which is a continuation-in-part of Ser. No. 746,649, Aug. 16, 1991, Pat. No. 5,208,281, which is a continuation-in-part of Ser. No. 651,271, Feb. 5, 1991, Pat. No. 5,167,882, which is a continuation-in-part of Ser. No. 632,391, Dec. 21, 1990, abandoned.

[51] Int. Cl.$^5$ ............ C08G 85/00; C08G 75/14; C08G 75/04
[52] U.S. Cl. .................. 528/376; 528/489; 522/78; 522/79; 522/180
[58] Field of Search ............ 522/180, 78, 83, 79; 528/489, 376

[56] References Cited

U.S. PATENT DOCUMENTS

| | | | |
|---|---|---|---|
| 3,445,419 | 5/1969 | Vanderlinde | 260/37 |
| 3,619,393 | 11/1971 | Stahly | 204/159.15 |
| 3,661,744 | 5/1972 | Kehr et al. | 204/159.14 |
| 3,923,748 | 12/1975 | Hutt et al. | 528/374 |
| 4,119,617 | 10/1978 | Hanyuda et al. | 528/360 |
| 4,125,644 | 11/1978 | Ketley et al. | 427/36 |
| 4,474,830 | 10/1984 | Taylor | 427/54.1 |
| 4,604,295 | 8/1986 | Humphreys | 522/60 |
| 4,765,712 | 8/1988 | Bohannon, Jr. et al. | 350/96.23 |
| 4,808,638 | 2/1989 | Steinkraus et al. | 522/84 |
| 4,913,859 | 4/1990 | Overton et la. | 264/1.4 |
| 4,935,455 | 6/1990 | Huy et al. | 522/99 |
| 4,946,874 | 8/1990 | Lee et al. | 522/14 |
| 4,956,198 | 9/1990 | Shama et al. | 427/54.1 |
| 4,962,992 | 10/1990 | Chapin et al. | 350/96.23 |
| 4,973,611 | 11/1990 | Puder | 522/42 |
| 5,026,409 | 6/1991 | Robinson et al. | 65/3.11 |
| 5,028,661 | 6/1991 | Clark et al. | 525/189 |
| 5,034,490 | 7/1991 | Jacobine et al. | 528/30 |
| 5,167,882 | 12/1992 | Jacobine et al. | 264/22 |
| 5,171,816 | 12/1992 | Jacobine et al. | 528/15 |
| 5,182,360 | 1/1993 | Jacobine et al. | 528/205 |
| 5,208,281 | 5/1993 | Glaser | 524/189 |

FOREIGN PATENT DOCUMENTS 0428342 5/1991 European Pat. Off. .

OTHER PUBLICATIONS

Product Data Sheet: "QO ® POLYMEG ® Polyols, General Information, Handling and Properties", QO Chemicals, Inc., 1990.
Abstract: "A New Derivation of Average Molecular Weights of Nonlinear Polymers", C. W. Macoski & D. R. Miller, Molecular Weights of Nonlinear Polymers, vol. 9, No. 2, Mar.–Apr. 1976.
Abstract: "Thermo–Oxidative Aging of a Primary Lightguide Coating in Films and Dual-Coating in Films and Dual-Coated Fibers", D. A. Simoff, M. G. Chan, J. T. Chapin & B. J. Overton, Polymer Engineering and Science, Mid–Sep. 1989, vol. 29, No. 17.
M. Atteya & K. Klabunde, "Nanoscale Metal Oxide Particles as Chemical Reagents", Chem. Mater. 1991, 3, 182–187.
B. Wagner & A. Kottenhahn, "Oxidative Addition of Mercaptans to Olefins in the Presence of a Halide", Chemische Berichte, vol. 93 (1960), pp. 2415–2423.
Abstract: "A Dynamic Modal for Optical-Fiber Coating Application", D. H. Smithgall, Journal of Lightwave Technology vol. 8, No. 10, Oct. 1990.
Abstract: "Fiber Optics: New Eyes of Industry", J. Holusha, The New York Times, Nov. 6, 1991.
Abstract: "Time-Temperature Dependence of Dual Coated Lightguide Pullout Measurements", B. J. Overton & C. R. Taylor, Polymer Engineering and Science, Mid–Sep. 1989, vol. 29, No. 17.

*Primary Examiner*—Susan W. Berman
*Attorney, Agent, or Firm*—Vidas, Arrett & Steinkraus

[57] ABSTRACT

A treatment method for polythiol compounds used in thiol-ene formulations, especially formulations employing norbornene resins, significantly improves cure speed retention on aging of thiol-ene formulations which include hydroxylamine salts, such as N-nitrosoarylhydroxylamine aluminum salts, as shelf-life stabilizers. The treatment comprises contacting the polythiol with an amphoteric treating agent selected from the group consisting of silicated magnesium oxide, magnesium oxide, magnesium hydroxide, calcium oxide, calcium hydroxide, barium oxide, and barium hydroxide, and then separating the resin from the treating agent prior to mixture with a polyene to form a thiol-ene composition. In formulations employing phenolic compounds having an alkenyl group in conjugation with the phenyl group thereof as shelf-life co-stabilizers the treatment method also significantly enhances the shelf-life stability of the formulation compared to formulations made from untreated polythiol.

24 Claims, No Drawings

THIOL-ENE COMPOSITIONS WITH IMPROVED CURE SPEED RETENTION

CROSS-REFERENCE TO RELATED APPLICATIONS

This application is a continuation-in-part of copending applications, Ser. No. 07/619;068, filed Nov. 28, 1990 and a continuation-in-part of Ser. No. 08/056;128, filed Apr. 30, 1993, incorporated herein by reference, which is a continuation-in-part of Ser. No. 07/746,649, filed Aug. 16, 1991, U.S. Pat. No. 5,208,281, incorporated herein by reference, which is a continuation-in-part of Ser. No. 651,271, filed Feb. 5, 1991, U.S. Pat. No. 5,167,882, incorporated herein by reference, which is a continuation-in-part of Ser. No. 632,391, filed Dec. 21, 1990, abandoned.

BACKGROUND OF THE INVENTION

1. Field of the Invention

The present invention pertains to a method for improving cure speed retention of thiol-ene formulations and to thiol-ene formulations with improved cure speed retention on aging.

2. Definitions

As used herein:

A polyene is a compound having a plurality of olefinically unsaturated groups.

A polythiol is a compound having plurality of organic thiol groups.

A thiol-ene composition is a mixture of a polyene and a polythiol formulated to cure at least predominately by addition of thiol groups across the olefinic double bond of the polyene.

Norbornenyl groups, as used herein, are broadly defined to encompass organic functional groups of the formula:

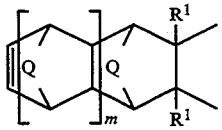

where Q is $CR_2^1$, O, S, $NR^1$ or $SO_2$, $R^1$ is H or alkyl; and m is 0–10. Thus the term should be understood to encompass, in addition to true norbornenyl groups, various substituted analogs, nadic groups and various other cyclopentadiene Diels-Alder polyadducts.

BACKGROUND ART

Thiol-ene formulations are known from Oswald, *Die Macromolekulare Chemie*, 97, 258–266 (1966); U.S. Pat. No. 3,661,744; and U.S. Pat. No. 4,119,617. In general, such formulations are mixtures of polythiol and polyene compounds which are cured by radical reaction to form a polythiol ether. Acid catalyzed cure is also described in the literature. The principle cure mechanism of interest for commercial products, however, has been the photoinitiated free radical cure mechanism.

In U.S. Pat. No. 4,808,638, incorporated herein by reference, there are described photocurable thiolene compositions comprising a norbornene functional resin, a polythiol and a free radical photoinitiator. Further description of this system may be found in Jacobine et al, *Proceedings of ACS Division of Polymeric Materials: Science and Engineering*, Vol. 60, pp. 211–216 (1989). Further norbornenyl functional compounds useful in thiol-ene compositions as described in U.S. Pat. No. 4,808,638, U.S. Pat. No. 5,034,490, U.S. Pat. No. 5,171,816 and U.S. Pat. No. 5,182,360 and copending applications Ser. No. 07/315,737 filed Feb. 24, 1989, now U.S. Pat. No. 5,266,670, and Ser. No. 07/619,068 filed Nov. 28, 1990.

Conventional free-radical stabilizers, such as hydroquinone, phenothiazine and the like, are commonly used as stabilizers for such thiol-ene formulations but it has long been recognized that such stabilizers often are not effective for providing a thiol-ene formulation with a commercially acceptable shelf-life. Even with careful packaging to exclude any light, thiol-ene formulations often polymerize in their package within a few weeks of manufacture. Dark stability of thiol-ene curable formulations has been a problem for a number of these systems, particularly those where the polyene is a plural norbornene compound. The norbornene-thiol system, however, is an especially desirable system because of its very high cure speed, good cured polymer properties and the ready availability of norbornene resins from acrylate ester precursors.

Various attempts have been made to improve upon the dark stability of thiol-ene systems by use of improved stabilizers. References pertaining to these efforts include U.S. Pat. No. 3,619,393; U.S. Pat. No. 5,208,281; and EP 428,342. In EP 428,342 it is disclosed that certain N-nitrosoarylhydroxyl amines and salts thereof are much superior stabilizers for radically curable norbornenyl/thiol formulations.

Further improvements on stabilization of thiol-ene systems, especially those employing norbornene functional polyenes, are described in U.S. Pat. No. 5,208,281 (in which polyiodide treatment of the formulation resin is disclosed) and in concurrently filed application, Ser. No. 08/081,456 of David M. Glaser, Anthony F. Jacobine and Paul J. Grabek, entitled "Stabilizer System for Thiol-Ene Compositions," (in which an alkenyl substituted phenolic compound, such as 2-propenylphenol, 4-acetoxy styrene, 2-allylphenol, isoeugenol, 2-ethoxy-5-propenylphenol, 2-allyl-4-methyl-6-t-butylphenol, 2-propenyl-4-methyl-6-t-butylphenol, 2-allyl-4,6-di-t-butylphenol, and 2,2'-diallylbisphenol A, and one or more compounds selected from the group consisting of a free radical scavenger, a hindered phenolic antioxidant and a hydroxylamine derivative are employed as shelf-life stabilizers). In both of these improved systems a N-nitrosoarylhydroxyl amine salt is desirably employed, particularly when the polyene is a norbornenyl functional polyene.

It has also recently been discovered that treatment of norbornene resins, prior to formulation with a polythiol, with an amphoteric treating agent selected from the group consisting of silicated magnesium oxide, basic aluminum oxide, silica gel magnesium oxide, magnesium hydroxide, calcium oxide, calcium hydroxide, barium oxide, and barium hydroxide, and then separating the resin from the treating agent can also significantly contribute to stabilization of certian problem formulations. Treatment of the thiol component has not been found to consistently impact the shelf-life stability of the formulations, however.

Thiol-ene systems stabilized with a hydroxylamine salt, such as a N-nitrosoarylhydroxylamine salt have been found to lose cure speed on aging at varying rates. Consequently, to obtain optimal benefits of the stabilization systems employing hydroxylamine salts, especially N-nitrosoarylhydroxylamine salts it is important to reduce the problem of cure speed loss on aging.

SUMMARY OF THE INVENTION

It has now been discovered that treatment of a polythiol, prior to mixture with a polyene to form a thiol-ene composition, significantly reduces the loss of cure speed on aging which has been observed with compositions stabilized with hydroxylamine salts. The treatment comprises contacting the polyene with an amphoteric treating agent selected from the group consisting of silicated magnesium oxide, magnesium oxide, magnesium hydroxide, calcium oxide, calcium hydroxide, barium oxide, and barium hydroxide, and then separating the resin from the treating agent.

In formulations stabilized with an alkenyl substituted phenolic compound as described above in which the alkenyl group is in conjugation with the aromatic ring, the thiol treatment has also been observed to further enhance shelf-life stability of the thiol-ene formulations.

The invention comprises in one aspect a radically curable thiol-ene formulation comprising a mixture of a polyene, a polythiol and a hydroxylamine salt shelf-life stabilizer characterized in that the polythiol has been treated with an amphoteric treating agent as described above. In another aspect the invention is a formulation as described, further comprising an alkenyl substituted phenolic compound in which the alkenyl group is in conjugation with the aromatic ring thereof. In a still further aspect the invention comprises a method of making a thiol-ene formulation in which the polythiol component of the formulation is treated with an amphoteric substance as described herein.

DETAILED DESCRIPTION OF THE INVENTION

The amphoteric substance used to treat the polythiol is selected from the group consisting of silicated magnesium oxide, magnesium oxide, magnesium hydroxide, calcium oxide, calcium hydroxide, barium oxide and barium hydroxide. The average particle size of the amphoteric substance is preferably in the range of about 2 microns to about 200 microns. A particularly preferred amphoteric agent is Magnesol®Polysorb 30/40 hydrated silicated magnesium oxide, which has a particle size range of from about 2 to about 200 microns and an average particle size of 50 microns.

Optimal contact time with the polythiol will vary depending upon the temperature employed and the moisture content and viscosity of the polythiol. The time should be sufficient time to improve the retention of cure time of the formulated thiol-ene composition. Typical contact times will be between 1 hour and 3 days. Treatment efficiency can be improved, lessening necessary contact time, if the polythiol has a small moisture content, suitably, 0.01%–1.0%. When a dry polythiol is used and moisture can readily be removed subsequent to treatment, e.g. by vacuum stripping, it may be desirable to add moisture to the treatment mixture. Preferably the treatment is conducted under nitrogen atmosphere but treatment in ambient air is also suitable.

Contact temperatures will also vary depending on viscosity of the polythiol. Effective treatment can be obtained at temperatures between 0° C. and 100° C., provided that the polythiol is sufficiently non-viscous at the temperature employed to allow for good agitation of the mixture.

The amphoteric treating agent is desirably removed from the polythiol prior to formulation into a curable composition, such as a thiol-ene composition. Separation can be accomplished by filtration but in some cases where the amphoteric treating agent has a clay-like consistency addition of a filter aid such as Celite ® to the treatment mixture prior to filtration is necessary for effective filtration. Addition of the filter aid does not appear to influence the effectiveness of the amphoteric treating agent in improving cure speed retention or shelf-life stability of thiol-ene compositions produced from the treated polythiol.

Extensive examples of polyenes useful in the inventive formulations are provided in U.S. Pat. No. 3,661,744, U.S. Pat. No. 4,119,617, U.S. Pat. No. 4,157,421, U.S. Pat. No. 4,808,638, and U.S. Pat. No. 5,021,512, all of which are incorporated herein by reference. Preferred polyenes are compounds containing a plurality of norbornene, vinyl or allylic groups.

Examples of norbornene functional compounds may be found in U.S. Pat. No. 4,808,638, U.S. Pat. No. 5,034,490, U.S. Pat. No. 5,167,882, U.S. Pat. No. 5,182,360, and in co-pending U.S. application Ser. No. 07/619,068 filed Nov. 28, 1990, all incorporated herein by reference. Preferred norbornene compounds are those which include groups of the formula:

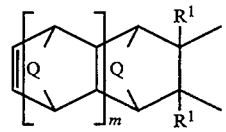

in which Q is CH$_2$, m is 0 and the R$^1$ groups are independently H or methyl, especially compounds having a plurality of groups of the formula

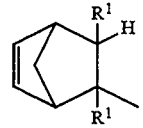

where R$^1$ is H or methyl. Particularly preferred norbornene compounds are norbornene carboxylate esters of polyols such as 1,6-hexanediol, trimethylolpropane, ethoxylated bisphenol A, OH-terminated poly(tetramethylene oxide) and mixtures thereof. Preferably the norbornene resin is treated with an amphoteric substance as described in U.S. application Ser. No. 08/056,128, filed Apr. 30, 1993.

The polythiol component of the inventive compositions may be any compound having two or more thiol groups per molecule. Suitable polythiols are described in U.S. 3,661,744 at Col. 8, line 76—Col. 9, line 46; in U.S. Pat. No. 4,119,617, Col. 7, lines 40–57; U.S. Pat. No. 3,445,419; and U.S. Pat. No. 4,289,867. Especially preferred are polythiols obtained by esterification of a polyol with an α or β-mercaptocarboxylic acid such as thioglycolic acid, or β-mercaptopropionic acid. Particularly preferred polythiols are trimethylolpropane-trimercaptoacetate, trimethylolpropane-trimercaptopropionate, pentaerythritol tetramercaptoacetate and pentaerythritol tetrakis-β-mercaptopropionate (PETMP). The polythiol may also be an oligomer of a tri, tetra or higher functional thiol compound and a polyene, suitably a dinorbornene compound, the oligomer prepared by reacting a sufficient deficiency of said polyene to provide an ungelled polythiol functional oligomer. Details of the calculations necessary to predict a suitable ratio of polythiol compound to polyene are provided in the concurrently filed application Ser. No. 08/080,748 of Anthony F. Jacobine, Steven T. Nakos, John G. Woods, Margaret Rakas, Louis Alberino, Philip Kropp, David M. Glaser and Donna Sutkaitis, entitled "*Optical Fiber Primary Coatings and Fibers Coated Therewith*," incorporated herein by reference.

The ratio of the polythiol to the polyene component can be varied widely. Generally it is preferred that the ratio of thiol to ene groups be between 0.8:1 and 1.3:1, more preferably about 1:1, but ratios outside this range may occasionally be usefully employed without departing from the invention hereof.

While a curable composition using compounds of the invention may include both difunctional ene compounds and difunctional thiol compounds, it will be understood that at least a portion of at least one of these components should ordinarily contain more than two functional groups per molecule so as to produce a crosslinked product when cured. That is, the total of the average number of ene groups per molecule of polyene and the average number of coreactive thiol groups per molecule of the polythiol should be greater than 4 when a crosslinked cured product is desired. This total is referred to as the "total reactive functionality" of the composition.

The thiol-ene formulations also include a hydroxylamine salt, most suitably an N-nitrosoarylhydroxylamine salt thereof as a shelf-life stabilizer. Illustrative examples being the ammonium, sodium, potassium, magnesium, strontium, aluminum, copper, zinc, cerium, iron, nickel and cobalt salts of N-nitrosophenylhydroxylamine. The aluminum salt of N-nitrosophenylhydroxylamine, sold under the tradename Q1301 by Wako Pure Chemical Industries, Hawthorne, N.Y., is preferred. Suitable levels of such inhibitors are between about 10 ppm and 2%, preferably 10–50,000 ppm. Other free radical inhibitors may also be useful in the invention, such as sulfur, phenothiazine, hydroquinone, butylated hydroxy toluene (BHT) and the like, at levels of between about 0.5% and 5%.

Preferably the formulations also include an alkenyl substituted phenolic compound, such as 2-propenylphenol, 4-acetoxy styrene, 2-allylphenol, isoeugenol, 2-ethoxy-5-propenylphenol, 2-allyl-4-methyl-6-t-butylphenol, 2-propenyl-4-methyl-6-t-butylphenol, 2-allyl-4,6-di-t-butylphenol, 2-propenyl-4,6-di-t-butylphenol and 2,2'-diallyl-bisphenol A, optionally additionally including a free radical scavenger or a hindered phenolic antioxidant, as described in concurrently filed application Ser. No. 08/081,456 of David M. Glaser, Anthony F. Jacobine and Paul J. Grabek, entitled "*Stabilizer System for Thiol-Ene Compositions*," incorporated herein by reference. When the alkenyl group of such phenolic compounds is in conjugation with the aromatic ring thereof it has been observed that the treatment method of the invention, in addition to improving cure speed retention, significantly further enhances shelf-life stability compared to similar formulations employing untreated polythiols. The alkenyl substituted phenolic compounds are suitably employed at levels of 200 ppm–15,000 ppm, preferably 500–7,000 ppm, based on the total weight of the formulation. Still more preferably the formulation also includes a free radical scavenger such as p-methoxyphenol (MEHQ), or a hindered phenolic antioxidant such as BHT, or both, at a level of 100–1000 ppm.

An initiator will usually be used in the curable thiolene formulations, suitably a free radical photoinitiator. Examples of free radical photoinitiators include benzoin and substituted benzoin compounds, benzophenone, Michler's ketone, dialkoxybenzophenones, dialkoxyacetophenones, peroxyesters described in U.S. Pat. Nos. 4,616,826 and 4,604,295, etc. The photoinitiator is employed in an amount effective for initiating cure of the formulation upon irradiation with UV light, suitably 0.1–10%, typically 0.5–5%. If electron beam curing is desired no initiator need be employed. If thermal curing is desired the formulation may employ a thermally activated free radical initiator such as a peroxy or azonitrile compound.

The invention is illustrated by reference to the following non-limiting examples.

EXAMPLES

Dinorbornene resins used in the examples were produced as described in co-pending application Ser. No. 08/056,068, filed Apr. 30, 1993.

TEST PROCEDURES

Relative Viscosity For Formulations

Relative viscosity's were taken on a Brookfield HBTD viscometer equipped with small sample adapter using sample holder 13R and spindle 21 (Brookfield Engineering Laboratories, Inc., Stoughton, Mass.). Weight out 9 grams of formulation into 13R sample holder. Place sample holder with formulation into water bath set at 25.0° C. for ~2 hours to allow sample to degas and equilibrate at 25.0° C. Then place sample holder into small sample adapter and attach spindle 21. Adjust speed to lowest setting (0.5), let system run for thirty minutes to allow it to come to equilibrium. Then turn speed to 20 take reading after it stabilizes, if reading is to high, >90 lowest speed until you get a reading less than 90, if reading is too low, <20 increase speed until you get a reading greater than 20, then record reading and speed. Viscosity is calculated by multiplying the reading times a factor. Factor is determined by viscometer, speed, spindle and sample holder used and is supplied by Brookfield.

Fixture Speed

Fixture speed was obtained using a Oriel Model 87331 (Oriel Corporation, Strafford, Conn.) six inch collimated UV source equipped with a 500 watt super high pressure Hg lamp. Output was adjusted and calibrated to 10 mw/cm$^2$ using a International Light Model IL 1700 radiometer (International Light, Newburyport, Mass.). Fixture sample was prepared by placing a small amount of formulation between two precleaned plain microscope slides (75 mm×25 mm×1 mm) with an overlap of 15 mm×25 mm with 0.0015" gap. The fixture sample assembly is then exposed to UV light for 0.1–200 seconds. The overflow of the formulation on all four sides are carefully removed with a razor blade after they were exposed to UV light. The UV exposed sample assembly is then attached to a fixed stand at one end and a one kilogram weight is suspended from the other end for sixty seconds. The sample is then measured to determine if the slides have moved less than one millimeter. The sample is considered fixtured if the slides have moved less than one millimeter. Several samples are tested at 0.1 second intervals up to 10 seconds and at 1 second intervals up to 200 seconds until the fixture time is determined.

PREMIXES

Premix 1:

Premix 1 was made by adding 52.00 grams 2-hydroxy-2-methyl-1-phenyl-propan-1-one (Darocur 1173) and 1.040 grams N-nitrosophenylhydroxylamine aluminum salt (Q1301) into a 60 milliliter glass amber bottle equipped with a mechanical stirrer The components were mixed for ~17 hours until the Q1301 was completely dissolved. The whole process was carried out excluding actinic radiation and under a nitrogen atmosphere.

Premix 2:

Premix 2 was made by adding 189.00 grams of ethoxylated bisphenol A di(norborn-2-ene-5-carboxylate) (EBPA-DN) to a 250 milliliter amber glass bottle, sealing the bottle and warming it up to 75° C. in a water bath. Removing the bottle from the water bath and then adding 0.1553 grams 2,6-di-tert-butyl-4-methylphenol (BHT) and then equipping the bottle with a mechanical stirrer and nitrogen blanket. The two components are then mixed vigorously together for one hour then the bottle is reheated in a water bath to 75° C. while mixing for an additional one hour until all solids are completely dissolved. The whole process was carried out excluding actinic radiation and under a nitrogen atmosphere.

Premix 3:

Premix 3 was made by adding 390.81 grams of EB-PA-DN to a 500 milliliter amber glass bottle, sealing the bottle and warming it up to 49° C. in a water bath. Removing the bottle from the water bath and then adding 0.1810 grams p-methoxyphenol (MEHQ) (Freshly ground with a mortar and pestle) and then equipping it with a mechanical stirrer. The two components are then mixed vigorously together for two hours until all solids are complete dissolved. The whole process was carried out excluding actinic radiation and under a nitrogen atmosphere.

Premix 4:

Premix 4 was made by adding 39.00 grams Darocur 1173 and 7.164 grams 2-propenylphenol into a 60 milliliter glass amber bottle equipped with a mechanical stirrer. The components were mixed for one hour. The whole process was carried out excluding actinic radiation and under a nitrogen atmosphere.

Premix 5:

Premix 5 was made by adding 867.17 grams pentaerythritol tetra(3-mercaptopropionate) (PETMP) and 1.300 grams Q1301 into a one liter amber glass bottle equipped with a mechanical stirrer. The two components were mixed together at room temperature for 21 hours until all of the Q1301 was completely dissolved. The whole process was carried out excluding actinic radiation and under a nitrogen atmosphere.

Premix 6:

Premix 6 was made by adding 45.50 grams Darocur 1173, 8.358 grams 2-propenylphenol and 1.375 grams BHT into a 60 milliliter glass amber bottle equipped with a mechanical stirrer. The components were mixed for 2.5 hours until the Q 1301 and BHT was completely dissolved. The whole process was carried out excluding actinic radiation and under a nitrogen atmosphere.

Premix 7:

Premix 7 was made by charging 48.00 grams Darocur 1173 and 2.40 grams Q1301 into a 60 milliliter amber glass bottle equipped with a mechanical stirrer. The components were mixed for 4 hours until the Q1301 was completely dissolved. Then 40.32 grams of the above solution is transferred to another 60 milliliter amber glass bottle equipped as above. MEHQ(0.6528 grams) and 2-propenylphenol(7.054 grams) is then added and mixed for four hours at room temperature until all solids are completely dissolved. The whole process was carried out excluding actinic radiation and under a nitrogen atmosphere.

Premix 8:

Premix 8 was made by adding 978.42 grams of EB-PA-DN and 33.28 grams of Premix 7 to a 1 liter amber glass bottle equipped with a mechanical stirrer. The two components are then mixed together vigorously for two hours. The whole process was carried out excluding actinic radiation and under a nitrogen atmosphere.

Premix 9:

Premix 9 was made by adding 255.07 grams of EB-PA-DN and 9.005 grams of Premix 7 to a 500 milliliter amber glass bottle equipped with a mechanical stirrer. The two components are then mixed together vigorously for two hours. The whole process was carried out excluding actinic radiation and under a nitrogen atmosphere.

Example 1

Thiol-ene formulation was prepared by adding 47.70 grams of Premix 2. 17.34 grams of pentaerythritol tetra(3-mercaptopropionate) used as received (WR Grace, Lexington, Mass.) and 1.33 grams of Premix 1 to a 120 milliliter amber glass bottle equipped with a mechanical stirrer and nitrogen blanket. The components were mixed together for 2 hours. The whole process was carried out excluding actinic radiation and under a nitrogen atmosphere. Formulation was measured for 0-Time fixture time using the Fixture Speed procedures described above. The formulation was then transferred to 30 milliliter amber glass bottles (15 to 20 grams), blanketed with nitrogen then sealed. The bottles were aged for 7 days at 40° C. Fixture time was measured for the aged formulation.

Example 2

Thiol-ene formulation was prepared by adding 47.68 grams of Premix 3, 17.34 grams of pentaerythritol tetra(3-mercaptopropionate) (as received) and 1.33 grams of Premix 1 to 120 milliliter amber glass bottle equipped with a mechanical stirrer. The components were mixed together for 2 hours. The whole process was carried out excluding actinic radiation and under a nitrogen atmosphere. Formulation was measured for 0-Time fixture time using the Fixture Speed procedures described above. The formulation was then transferred to 30 milliliter amber glass bottles (15 to 20 grams), blanketed with nitrogen then sealed. The bottle was aged for 7 days at 49° C. Fixture time was measured for the aged formulation.

Example 3

Thiol-ene formulation was prepared by adding 47.66 grams of EBPA-DN, 17.37 grams of Premix 5 and 1.54 grams of Premix 4 to a 120 milliliter amber glass bottle equipped with a mechanical stirrer. The components were mixed together for 2 hours. The whole process was carried out excluding actinic radiation and under a nitrogen atmosphere. Formulation was measured for 0-Time fixture time using a Fixture Speed procedures described above. The formulation was then transferred to 30 milliliter amber glass bottles (15 to 20 grams), purged with nitrogen then sealed. The bottles were aged for 7 days at 49° C. Fixture time was measured for the aged formulation.

Example 4

Thiol-ene formulation was prepared by adding 47.66 grams of EBPA-DN, 17.34 grams PETMP and 1.54 grams of Premix 6 to a 120 milliliter amber glass bottle equipped with a mechanical stirrer. The components were mixed together for 2 hours. The whole process was carried out excluding actinic radiation and under a nitrogen atmosphere. Formulation was measured for 0-Time fixture time using the Fixture Speed procedures described above. The formulation was then transferred to 30 milliliter amber glass bottles (15 to 20 grams), purged with nitrogen and then sealed. The bottle was aged for 7 days at 49° C. Fixture time was measured for the aged formulation.

Example 5

Thiol-ene formulation was prepared by adding 47.68 grams of Premix 3.17.34 grams of PETMP and 1.54 grams of Premix 4 to a 120 milliliter amber glass bottle equipped with a mechanical stirrer. The components were mixed together for 2 hours. The whole process was carried out excluding actinic radiation and under a nitrogen atmosphere. Formulation was measured for 0-Time fixture time using the Fixture Speed procedures described above. The formulation was then transferred to 30 milliliter amber glass bottle (15 to 20 grams), purged with nitrogen and then sealed. The bottle was aged for 7 days at 40° C. Fixture time was measured for the aged formulation.

TREATMENT OF THIOLS

Treatment 1

Charge 1,000 grams of pentaerythritol tetra-(3-mercaptopropionate) into a one liter amber glass bottle equipped with a mechanical stirrer. Charge 30.92 grams of Celite ® 503 ® into the bottle then mix for 1 hour at room temperature under a nitrogen atmosphere. Then pour the contents of the bottle into a 4 liter stainless steel Seitz filer model 14B (Seitz Engineering Company, Kingstonn N.Y.) equipped with a one micron filer pad. The Seitz filter is then pressurized with 50 psi. nitrogen. The product (800 grams) is collected as a clear filtrate.

Treatment 2

Charge 1,000 grams of pentaerythritol tetra-(3-mercaptopropionate) into a one liter amber glass bottle equipped with a mechanical stirrer. Charge 20.4 grams of Magnesol Polysorb ® 30/40 into the bottle then mix for 4 hours at room temperature under a nitrogen atmosphere then add 10.1 grams of Celite ® 503 and mix for one additional hour. Then pour the contents of the bottle into 4 liter stainless steel Seitz filer model 14B (Seitz Engineering Company, Kingstonn N.Y.) equipped with one micron filter pad. The Seitz filter is then pressurized with 50 psi. nitrogen. The product (800 grams) is collect as a clear filtrate.

Treatment 3

Charge 1,000 grams of trimethylopropane tri-(3-mercaptopropionate) (TMP-TMP) into a one liter amber glass bottle equipped with a mechanical stirrer and nitrogen blanket. Charge 20.4 grams of Magnesol Polysorb ® 30/40 into the bottle then mix for 4 hours at room temperature under a nitrogen atmosphere then add 10.1 grams of Celite ® 503 and mix for one additional hour. Then pour the contents of the bottle into 4 liter stainless steel Seitz filter model 14B (Seitz Engineering Company, Kingstonn, N.Y.) equipped with a one micron filter pad. The Seitz filter is then pressurized with 50 psi. nitrogen. The product (800 grams) is collected as a clear filtrate.

Example 6

Thiol-ene formulation was prepared by adding 91.0 grams of Premix 8 and 32.02 grams of pentaerythritol tetra-(3-mercaptopropionate) used as received to a 120 milliliter amber glass bottle equipped with a mechanical stirrer. The components are mixed together for 2 hours. The whole process was carried out excluding actinic radiation and under a nitrogen atmosphere. Formulation was measured for 0-Time relative viscosity and fixture time using the Relative Viscosity and Fixture Speed procedures described above. The formulation was then transferred to two 30 milliliter amber glass bottles (15 to 2 grams), blanketed with nitrogen then sealed. The bottles were aged for 7 days at 49° C. and 91 days at room temperature. The viscosity and fixture time was measured for the aged samples.

Example 7

Thiol-ene formulation was prepared by adding 91.0 grams of Premix 8 and 32.02 grams of pentaerythritol tetra(3-mercaptopropionate) from Treatment 1 to a 120 milliliter amber glass bottle equipped with a mechanical stirrer. The components are mixed together for 2 hours. The whole process was carried out excluding actinic radiation and under a nitrogen atmosphere. Formulation was measured for 0-Time relative viscosity and fixture time using the Relative Viscosity and Fixture Speed procedures described above. The formulation was then transferred to two 30 milliliter amber glass bottles (15 to 20 grams), purged with nitrogen then sealed. The bottles were aged for 7 days at 49° C. and 91 days at room temperature. The viscosity and fixture time was measured for the aged samples.

Example 8

Thiol-ene formulation was prepared by adding 91.0 grams of Premix 8 and 32.02 grams of pentaerythritol tetra (3-mercaptopropionate) from Treatment 2 to a 120 milliliter amber glass bottle equipped with a mechanical stirrer and nitrogen blanket. The components are mixed together for 2 hours. The whole process was carried out excluding actinic radiation and under a nitrogen atmosphere. Formulation was measured for 0-Time relative viscosity and fixture time using the Relative Viscosity and Fixture Speed procedures described above. The formulation was then transferred to two 30 milliliter amber glass bottles (15 to 20 grams), purged with nitrogen then sealed. The bottles were aged for 7 days at 49° C. and 91 days a room temperature. The viscosity and fixture time was measured for the ages samples.

Example 9

Thiol-ene formulation was prepared by adding 88.03 grams of Premix 9 and 34.98 grams of trimethylolpropane tri-(3-mercaptopropionate) used as received to a 120 milliliter amber glass bottle equipped with a mechanical stirrer. The components are mixed together for 2 hours. The whole process was carried out excluding actinic radiation and under a nitrogen atmosphere. Formulation was measured for 0-Time relative viscosity and fixture time using the Relative Viscosity and Fixture Speed procedures described above. The formulation was then transferred to two 30 milliliter amber glass bottles (15 to 20 grams), purged with nitrogen then sealed. The bottles were aged for 7 days at 49° C. and 91 days at room temperature. The viscosity and fixture time was measured for the aged samples.

Example 10

Thiol-ene formulation was prepared by adding 88.03 grams of Premix 9 and 34.98 grams of trimethylolpropane tri-(3-mercaptopropionate) from Treatment 3 to a 120 milliliter amber glass bottles equipped with a mechanical stirrer. The components are mixed together for 2 hours. The whole process was carried out excluding actinic radiation and under a nitrogen atmosphere. Formulation was measured for 0-Time, relative viscosity and fixture time using the Relative Viscosity and Fixture Speed procedures described above. The formulation was then transferred to two 30 milliliter amber glass bottles (15 to 20 grams), purged with nitrogen then sealed. The bottles were aged for 7 days at 49° C. and 91 days at room temperature. The viscosity and fixture time was measured for the aged samples.

TABLE 1

EFFECTS OF COMBINATIONS OF BHT/MEHQ/2-PP/Q1301 ON FIXTURE TIMES OF THIOL-ENE FORMULATIONS

| | EXAMPLE NUMBER | | | | |
|---|---|---|---|---|---|
| | 1 | 2 | 3 | 4 | 5 |
| EBPA-DN | 47.66 | 47.66 | 47.66 | 47.66 | 47.66 |
| PETMP | 17.34 | 17.34 | 17.34 | 17.34 | 17.34 |
| DAROCUR 1173 | 1.30 | 1.30 | 1.30 | 1.30 | 1.30 |
| Q1301 | 0.0260 | 0.0260 | 0.0260 | — | — |
| BHT | 0.0392 | — | — | 0.0392 | — |
| MEHQ | — | 0.0221 | — | — | 0.0221 |
| 2-PROPENYLPHENOL | — | — | 0.2388 | 0.2388 | 0.2388 |
| LEVELS | | | | | |
| DAROCUR 1173 | 1.96 Wt % | 1.97 Wt % | 1.95 Wt % | 1.96 Wt % | 1.95 Wt % |
| Q1301 | 392 ppm | 392 ppm | 391 ppm | — | — |
| BHT | 591 ppm | — | — | 589 ppm | — |
| MEHQ | — | 333 ppm | — | — | 332 ppm |
| 2-PROPENYLPHENOL | — | — | 3,587 ppm | 3,587 ppm | 3,587 ppm |
| UV CURE SPEED, FIXTURE TIME*, 0.0015"-GAP, 10 mw/cm2 | | | | | |
| UV CURE, 0-TIME, 0.0015"-GAP, FIXTURE | 1.5 | 1.3 | 2.3 | 2.5 | 1.6 |
| UV CURE, 7-DAYS AT 49° C., 0.0015"-GAP, FIXTURE | 5.1 | 6.1 | 7.1 | 3.2 | 2.1 |
| % LOSS IN CURE SPEED | +240% | +369% | +209% | +28% | +31% |

TABLE 2

COMPARISON OF THE EFFECTS OF TREATMENT OF THIOL ON CURE SPEED AND STABILITY OF THIOLNENE FORMULATIONS

| | EXAMPLE NUMBER | | | | |
|---|---|---|---|---|---|
| | 6 | 7 | 8 | 9 | 10 |
| EBPA-DN | 88.01 | 88.01 | 88.01 | 85.03 | 85.03 |
| PETMP | 32.02 | — | — | — | — |
| PETMP, (Treated with 2 Wt % Magnesol Polysorb 30/40) | — | — | 32.02 | — | — |
| PETMP, (treated with 3 Wt % Celite 503) | — | — | — | — | — |
| TMP-TMP | — | — | — | 34.98 | — |
| TMP-TMP, (Treated with 2 Wt % Magnesol Polysorb 30/40) | — | — | — | — | 34.98 |
| DAROCUR 1173 | 2.39 | 2.39 | 2.39 | 2.40 | 2.40 |
| Q1301 | 0.1197 | 0.1197 | 0.1197 | 0.1200 | 0.1200 |
| 2-PROPENYLPHENOL | 0.4397 | 0.4397 | 0.4397 | 0.4409 | 0.4409 |
| METHYLHYDROQUINONE | 0.0407 | 0.0407 | 0.0407 | 0.0408 | .0408 |
| TREATMENT OF THIOL | AS RECEIVED | 3 Wt % CELITE 503 | 2 Wt % MAGNESOL POLYSORB 30/40 NOTE 1: | AS RECEIVED | 2 Wt % MAGNESOL POLYSORB 30/40 NOTE 1: |
| LEVELS | | | | | |
| DAROCUR 1173 (10171) | 1.95 Wt % | 1.95 Wt % | 1.95 Wt % | 1.99 Wt % | 1.99 Wt % |
| Q1301 (21067) | 992 ppm | 992 ppm | 992 ppm | 976 ppm | 976 ppm |
| 2-PROPENYLPHENOL (2-PP) | 3,574 ppm | 3,574 ppm | 3,574 ppm | 3,584 ppm | 3,584 ppm |
| MEHQ, Methylhydroquinone | 331 ppm | 331 ppm | 331 ppm | 332 ppm | 332 ppm |
| STABILITY DATA | | | | | |
| STARTING VISCOSITY, 0-TIME, cps | 6,700 | 6,912 | 6,740 | 3,460 | 3,485 |
| AGED VISCOSITY, 91 DAYS @ RT, cps | 8,040 | 8,145 | 7,260 | 3,960 | 3,661 |
| AGED VISCOSITY, 7 DAYS @ 49° C., cps | 9,360 | 9,438 | 7,500 | 4,420 | 3,818 |
| VISCOSITY GAIN AFTER 91 DAYS @ RT | 20% | 18% | 8% | 14% | 5% |
| VISCOSITY GAIN AFTER 7 DAYS @ 490° C. | 40% | 37% | 11% | 28% | 10% |

TABLE 2-continued

COMPARISON OF THE EFFECTS OF TREATMENT OF THIOL
ON CURE SPEED AND STABILITY OF THIOLNENE FORMULATIONS

UV CURE SPEED, FIXTURE TIME, 0.0015"-GAP, 10 mw/CM$^2$

| | | | | | |
|---|---|---|---|---|---|
| UV CURE, 0-TIME, 0.0015"-GAP, FIXTURE | 3.6 | 3.5 | 3.5 | 8.7 | 8.8 |
| UV CURE, 7-DAYS AT 49° C., 0.0015"-GAP, FIXTURE | 8.1 | 8.6 | 3.8 | 16.4 | 8.9 |
| UV CURE, 91 DAYS AT RT, 0.0015"-GAP, FIXTURE | 12 | 12 | 4.2 | 17.0 | 10.0 |
| % LOSS IN CURE SPEED AFTER 7 DAYS AT 49 C. | 125% | 146% | 11% | 89% | 1% |
| % LOSS IN CURE SPEED AFTER 91 DAYS AT RT | 233% | 243% | 20% | 95% | 14% |

NOTE 1: Celite 503 (1 Wt %) was added to all Magnesol Polysorb 30/40 treated thiols as filter aid.

What is claimed is:

1. A method of preparing a thiol-ene composition comprising:
    contacting a polythiol with an amphoteric treating agent selected from the group consisting of silicated magnesium oxide, magnesium oxide, magnesium hydroxide, calcium oxide, calcium hydroxide, barium oxide, and barium hydroxide;
    separating the polythiol from the treating agent; and then,
    mixing the polythiol with a polyene and a shelf-life stabilizer comprising a hydroxylamine salt.

2. A method as in claim 1 wherein the treating agent has a particle size between 2 microns and 200 microns.

3. A method as in claim 1 wherein the polyene is a compound having a plurality of norbornene groups thereon.

4. A method as in claim 1 wherein the polyene is a compound having a plurality of allyl or vinyl groups thereon.

5. A method as in claim 1 wherein the amphoteric treating agent is silicated magnesium oxide.

6. A method as in claim 1 wherein the polythiol is an oligomer of a compound having a plurality of norbornene groups thereon and a stoichiometric excess of a compound having at least three thiol groups per molecule.

7. A method as in claim 1 wherein the polythiol is selected from the group consisting of trimethylolpropane-tri-mercaptoacetate, trimethylolpropane-trimercaptopropionate, pentaerythritol tetramercaptoacetate and pentaerythritol tetrakis-β-mercaptopropionate.

8. A method as in claim 1 wherein the shelf-life stabilizer further comprises an alkenyl substituted phenolic compound.

9. A method as in claim 8 wherein the alkenyl group of said phenolic compound is in conjugation with the phenyl ring thereof.

10. A method as in claim 8 wherein said phenolic compound is selected from the group consisting of 2-propenylphenol, 4-acetoxy styrene, 2-allylphenol, isoeugenol, 2-ethoxy-5-propenylphenol, 2-allyl-4-methyl-6-t-butylphenol, 2-propenyl-4-methyl-6-t-butylphenol, 2-allyl-4,6-di-t-butylphenol, and 2,2'-diallyl-bisphenol A.

11. A method as in claim 1 wherein said contacting step is conducted for at least one hour at a temperature of between 0° C. and 100° C.

12. A method as in claim 1 wherein the hydroxylamine salt is a N-nitrosoarylhydroxylamine salt.

13. A method as in claim 12 wherein the N-nitrosoarylhydroxylamine salt is an aluminum salt.

14. A thiol-ene composition comprising:
    a polyene;
    a polythiol; and
    a stabilizer system comprising a hydroxylamine salt, wherein the polythiol has been treated by contacting it with an amphoteric treating agent selected from the group consisting of silicated magnesium oxide, magnesium oxide, magnesium hydroxide, calcium oxide, calcium hydroxide, barium oxide, and barium hydroxide.

15. A composition as in claim 14 wherein the polyene is a compound having a plurality of norbornene groups thereon.

16. A composition as in claim 14 wherein the polyene is a compound having a plurality of allyl or vinyl groups thereon.

17. A composition as in claim 14 wherein the amphoteric treating agent is silicated magnesium oxide.

18. A composition as in claim 14 wherein the polythiol is an oligomer of a plural norbornene compound and a stoichiometric excess of a compound having at least three thiol groups per molecule.

19. A composition as in claim 14 wherein the polythiol is selected from the group consisting of trimethylolpropane-tri-mercaptoacetate, trimethylolpropane-trimercaptopropionate, pentaerythritol tetramercaptoacetate and pentaerythritol tetrakis-β-mercaptopropionate.

20. A composition as in claim 14 wherein the shelf-life stabilizer further comprises an alkenyl substituted phenolic compound.

21. A composition as in claim 20 wherein the alkenyl group of said phenolic compound is in conjugation with the phenyl ring thereof.

22. A composition as in claim 20 wherein said phenolic compound is selected from the group consisting of 2-propenylphenol, 4-acetoxy styrene, 2-allylphenol, isoeugenol, 2-ethoxy-5-propenylphenol, 2-allyl-4-methyl-6-t-butylphenol, 2-propenyl-4-methyl-6-t-butylphenol, 2-allyl-4,6-di-t-butylphenol, and 2,2'-diallylbisphenol A.

23. A composition as in claim 14 wherein the hydroxylamine salt is a N-nitrosoarylhydroxylamine salt.

24. A composition as in claim 23 wherein the N-nitrosoarylhydroxylamine salt is an aluminum salt.

* * * * *